(12) United States Patent
Harrison et al.

(10) Patent No.: US 6,867,171 B2
(45) Date of Patent: Mar. 15, 2005

(54) LOW MOLECULAR WEIGHT BRANCHED ALKENYL SUCCINIC ACID DERIVATIVES PREPARED FROM LOW MOLECULAR WEIGHT POLYISOBUTENE AND UNSATURATED ACIDIC REAGENTS

(75) Inventors: James J. Harrison, Novato, CA (US); Kenneth Nelson, Clearlake, CA (US)

(73) Assignee: Chevron Oronitz Company LLC, San Ramon, CA (US)

( * ) Notice: Subject to any disclaimer, the term of this patent is extended or adjusted under 35 U.S.C. 154(b) by 144 days.

(21) Appl. No.: 10/305,901

(22) Filed: Nov. 27, 2002

(65) Prior Publication Data
US 2004/0102338 A1 May 27, 2004

(51) Int. Cl.[7] ............................ C10M 129/02; C10L 1/14
(52) U.S. Cl. ....................... 508/291; 508/293; 508/306; 508/496; 508/506; 508/551; 44/347; 44/348; 44/351; 44/389; 44/404; 44/418; 162/135; 548/546; 549/233
(58) Field of Search ................................ 508/306, 287, 508/291, 293

(56) References Cited

U.S. PATENT DOCUMENTS

| | | |
|---|---|---|
| 3,102,064 A | 8/1963 | Wurzburg et al. |
| 3,189,544 A | 6/1965 | Ratner et al. |
| 3,361,673 A | 1/1968 | Stuart et al. |
| 3,476,774 A | 11/1969 | Zaweski et al. |
| 3,819,660 A | 6/1974 | Cahill |
| 4,152,499 A | 5/1979 | Boerzel et al. |
| 4,225,447 A * | 9/1980 | Law et al. ................ 508/306 |
| 4,605,808 A | 8/1986 | Samson |
| 5,055,607 A * | 10/1991 | Buckley, III ............ 560/158 |
| 5,137,980 A | 8/1992 | DeGonia et al. |
| 5,175,225 A | 12/1992 | Ruhe, Jr. |
| 5,777,025 A | 7/1998 | Spencer et al. |
| 6,156,850 A | 12/2000 | Harrison et al. |
| 6,355,839 B1 | 3/2002 | Onopchenko |
| 6,451,920 B1 * | 9/2002 | Harrison et al. ......... 525/327.4 |
| 6,617,396 B1 * | 9/2003 | Harrison et al. ......... 525/301 |

FOREIGN PATENT DOCUMENTS

| | | |
|---|---|---|
| EP | 1 316 564 A2 | 6/2003 |
| GB | 2 081 722 A | 2/1982 |
| WO | WO 91/04959 | 4/1991 |

OTHER PUBLICATIONS

R.W. Davison, The sizing of paper, Tappi/Mar., 1975; vol. 58, No. 3: 10 pages. R.W. Davison, Research Scientist, Hercules Inc., Wilmington, Delaware 19899.

* cited by examiner

*Primary Examiner*—Ellen M McAvoy
(74) *Attorney, Agent, or Firm*—Josetta I. Jones; Claude Caroli

(57) ABSTRACT

This invention is directed to a new low molecular weight branched alkenyl succinic acid derivative that may be prepared by reacting a low molecular weight polyisobutene (PIB) having from about 8 to about 32 carbon atoms, and wherein at least about 50% of the olefinic bonds of the polyisobutene comprises methylvinylidene isomer plus tri-substituted isomer, with an unsaturated acidic reagent and method of making same, resulting in alkenyl succinic acid derivative isomers; and a low molecular weight branched alkenyl succinimide and method of making same.

37 Claims, No Drawings

LOW MOLECULAR WEIGHT BRANCHED ALKENYL SUCCINIC ACID DERIVATIVES PREPARED FROM LOW MOLECULAR WEIGHT POLYISOBUTENE AND UNSATURATED ACIDIC REAGENTS

BACKGROUND OF THE INVENTION

It is well known in the art that alkenylsuccinic anhydrides (ASAs) made from alpha olefins and maleic anhydride are useful as paper sizing agents in the paper industry. Paper sizing is the treatment of the cellulose fibers of paper so that the paper is resistant to liquid wetting. ASAs made from alpha olefins suffer from the drawback that they are solids which often require that they be melted or dissolved in a suitable solvent before use. It would be much easier to handle these materials if they were liquids. ASAs made from isomerized alpha olefins are generally liquids but the synthesis of ASAs from isomerized alpha olefins requires an additional olefin isomerization step.

This invention is directed to new low molecular weight branched alkenyl succinic acid derivatives (ASAD) that may be prepared by reacting a low molecular weight polyisobutene (PIB) having less than about 32 carbon atoms with an unsaturated acidic reagent. The low molecular weight branched alkenyl succinic acid derivative may be useful as is, or as an intermediate for (1) low molecular weight branched succinimides, (2) detergents or dispersants for lube oil or fuels, (3) pour point depressants, (4) surface sizing agents for paper and (5) friction modifiers for automatic transmission fluids and continuous variable transmissions (CVTs). The low molecular weight branched ASAD may be used by itself or as the ester, amide, imide or metal salt derivative of the low molecular weight branched ASAD. Preferred low molecular weight branched ASADs are liquid at ambient temperature.

It is known that olefin/unsaturated acidic reagent ASA compositions may be prepared by reacting an olefin with an unsaturated acidic reagent thermally. This reaction is typically carried out at elevated temperatures either neat or in a solvent or diluent.

One drawback to using an alpha olefin to prepare the ASA is that the resulting ASA is typically a glassy solid. A solid ASA is undesirable because a solid ASA cannot be handled easily or pumped readily at ambient temperatures. Before further processing, a solid ASA has to be brought to a consistency that may be pumped readily. Achieving such a consistency may be accomplished by heating the solid ASA to a temperature above the melting point or using a solvent to dissolve it. Heating the ASA is often costly, and the addition of a solvent is often not practical because it is desirable to remove the solvent before the ASA can be used; furthermore, the solvent has to be disposed of in a manner consistent with environmental regulations.

Additionally, in order to make a liquid product, alpha olefins can be reacted with reagents that isomerize the double bond to an internal position in the alkyl chain. When this isomerized olefin reacts with the unsaturated acidic reagent to form an ASA, the desired ASA is usually a liquid at room temperature. The addition of such an isomerization step is often costly and thus undesirable.

The low molecular weight branched ASAD of this invention is an improvement over alpha olefin ASAs. Since the low molecular weight branched ASAD of this invention is liquid, it is not necessary to dissolve the low molecular weight branched ASAD by using additional heat or adding solvent before the low molecular weight branched ASAD is used. Since no solvent is required, the step of removing the solvent is not necessary either. Also the need to isomerize the olefin to an internal olefin position, which is an additional step and can increase the cost of production of the ASAD, is not necessary for the production of the low molecular weight branched ASAD of this invention.

Boerzel et al., U.S. Pat. No. 4,152,499, disclose isobutene polymers having a degree of polymerization of from 10 to 100, where the proportion of theoretically possible terminal double bonds is greater than in conventional polybutene products.

Samson, U.S. Pat. No. 4,605,808, discloses a process for cationic polymerization of 1-olefins, particularly isobutene, thereby producing polyisobutenes with a relatively high degree of terminal unsaturation and having a molecular weight of between 500 and 5000. The high proportion of terminal unsaturation in the polyisobutene polymers are particularly suited for producing adducts with maleic anhydride.

Wurzburg et al., U.S. Pat. No. 3,102,064, disclose using substituted cyclic dicarboxylic acid anhydrides as paper sizing agents.

Onopchenko, U.S. Pat. No. 6,355,839 discloses a process for the preparation of alkylated diphenylamine antioxidant which comprises alkylating diphenylamine with polyisobutene in the presence of a clay catalyst, wherein the polyisobutylene has an average molecular weight in the range of 120 to 600 and wherein the polyisobutylene contains at least 25% methylvinylidene isomer.

DeGonia et al., U.S. Pat. No. 5,137,980, disclose the formation of polybutenyl succinic acids or acid derivatives that are useful in the manufacture of polybutenyl succinic acid esters, polybutenyl succinimides or succinamides, and polybutenyl succinic ester-amides by reaction with alcohols or amines, or combinations thereof.

Harrison et al., U.S. Pat. No. 6,156,850, disclose a process for the preparation of a polyalkyenyl derivative of an unsaturated acidic reagent. Specifically, the reaction is started in the absence of a strong acid. The strong acid is later added when at least 25% of the polyalkene is converted to a polyalkenyl derivative of an unsaturated acidic reagent.

Ratner et al., U.S. Pat. No. 3,189,544, disclose highly detergent non-ash forming mineral lubricating oil compositions. A small amount of an oil-soluble organic sulfonic acid salt of amino-imide of a long-chain monosubstituted polymeric hydrocarbyl succinic anhydride is added to lubricating oils. The long-chain polymeric substituent may be straight or branched chain and derived from olefins of from 2 to 8 carbon atoms such as ethylene, proplylene, 1-butene, isobutene, 1-hexene, styrene, alpha methyl-styrene and copolymers thereof, of from 20 to 500 carbon atoms and a molecular weight of 300 to 5000.

Ruhe, Jr., U.S. Pat. No. 5,175,225, discloses a process for preparing an oligomeric copolymer of an unsaturated acidic reactant and a high molecular weight olefin having a sufficient number of carbon atoms such that the resulting copolymer is soluble in lubricating oil and wherein at least 20 weight percent of the total olefin comprises and alkylvinylidene isomer, which process comprises reacting the high molecular weight olefin with the unsaturated acidic reactant in the presence of a free radical initiator and a solvent which comprises the reaction product of an unsaturated acidic reactant and a high molecular weigh olefin.

Zaweski, et al., U.S. Pat. No. 3,476,774, disclose a process for producing an olefinically substituted carboxylic acid or derivative by the reaction of an olefin with an alpha, beta-unsaturated carboxylic acid or derivative.

Cahill et al., U.S. Pat. No. 3,819,660 disclose suppressing fumaric acid sublimation and tar formation during reaction of 168 to 900 molecular weight alkene with maleic anhydride and increased yield of alkenylsuccinic anhydride by the use of catalytic amount of p-alkenylbenzenesulfonic acid.

Spencer et al., U.S. Pat. No. 5,777,025, disclose reacting $C_4$–$C_{10}$ dicarboxylic acid with a polyalkene at high temperature and under high inert gas partial pressure in the presence of a sediment-inhibiting amount of hydrocarbyl substituted sulfonic acid.

Davison, R. W., "The Sizing of Paper," TAPPI, Vol. 58, No. 3 (March 1975) pp. 48–57, summarizes qualities of paper sizing agents.

SUMMARY OF THE INVENTION

This invention is directed to new low molecular weight branched ASADs that may be prepared by reacting a low molecular weight polyisobutene (PIB) having less than about 32 carbon atoms, wherein the polyisobutene contains at least 50% of the methylvinylidene isomer plus tri-substituted isomer, and a number average molecular weight less than 450, with an unsaturated acidic reagent. The low molecular weight branched ASAD may be useful as is, or as an intermediate for (1) low molecular weight branched succinimides, (2) detergents or dispersants for lube oil or fuels, (3) pour point depressants, (4) surface sizing agents for paper, and (5) friction modifiers for automatic transmission fluid and continuous variable transmissions (CVTs). The low molecular weight branched ASAD may be used by itself or as the ester, amide, imide, or metal salt derivative of the low molecular weight branched ASAD. The preferred low molecular weight branched ASAD is liquid at ambient temperature.

This invention comprises one or more low molecular weight branched alkenyl succinic acid derivatives having the formula:

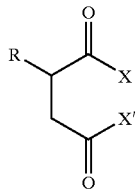

(A)

wherein X and X' are independently selected from the group consisting of: —OH; —OR$^1$, wherein R$^1$ is alkyl of 1 to 8 carbon atoms; —NH$_2$; —Cl; —Br; and —OM+, wherein M+ is the equivalent of at least one of a metal, ammonium or alkyl ammonium cation wherein the alkyl group has 1 to 8 carbon atoms; and X and X' when taken together are —O— or —NH—; R is a polyisobutenyl group or a mixture of low molecular weight polyisobutenyl groups having from about 8 to about 32 carbon atoms, preferably from about 12 to about 28 carbon atoms, derived from a polyisobutene having at least 50% of the methylvinylidene isomer plus tri-substituted isomer. The low molecular weight branched ASAD may further be reacted to form one or more of an amide derivative, an ester derivative, an imide derivative and a metal salt derivative.

The low molecular weight branched ASAD may be prepared by the reaction of one or more unsaturated acidic reagents and one or more polyisobutenes having from about 8 to about 32 carbon atoms, preferably from about 12 to about 28 carbon atoms and at least 50% of the methylvinylidene isomer plus tri-substituted isomer content. The reaction may be carried out thermally or may be catalyzed by the presence of strong acids. The unsaturated acidic reagent may comprise maleic anhydride. The polyisobutene may comprise a mixture further comprising about 5 wt. % to about 20 wt. % $C_8H_{16}$; about 35 wt. % to about 55 wt. % $C_{12}H_{24}$; about 20 wt. % to about 30 wt. % $C_{16}H_{32}$; about 8 wt. % to about 15 wt. % $C_{20}H_{40}$; about 2 wt % to about 8 wt % $C_{24}H_{48}$; and about 0.5 wt % to about 2 wt. % $C_{28}H_{56}$. The low molecular weight PIBs have an average molecular weight of about 450 or less. Preferred low molecular weight PIBs have an average molecular weight of about 120 to about 392. More preferred low molecular weight PIB has a molecular weight of about 120 to about 300. Preferably, the methylvinylidene isomer content of the low molecular weight PIB will be at least 40%, more preferably, at least 50%, and even more preferably, at least 60%.

Preferably, the low molecular weight branched ASAD of this invention may also comprise one or more double bond isomers having the general formula:

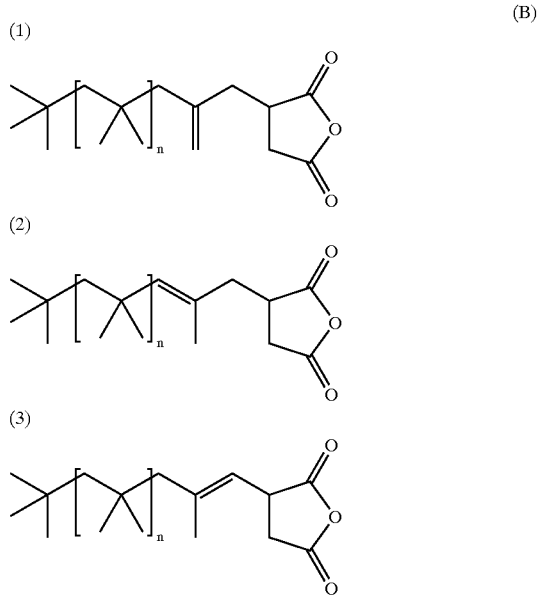

(B)

wherein n is a whole integer from 1 to 6.

This invention may also comprise one or more succinimides having the general formula of:

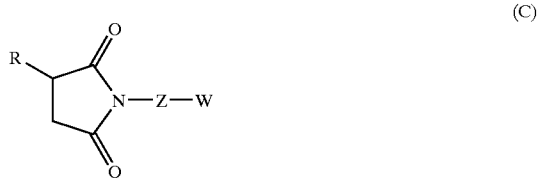

(C)

wherein W comprises one or more of:

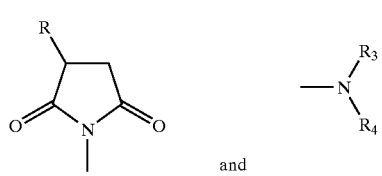

(D)

and wherein R is a polyisobutenyl group having from about 8 to about 32 carbon atoms or a mixture of low molecular weight polyisobutenyl groups having from about 8 to about 32 carbon atoms derived from a polyisobutene having at least 50% of the methylvinylidene isomer plus tri-substituted isomer; Z is one or more polyamine linking radicals; and wherein R$_3$ and R$_4$ are independently hydrogen, alkyl of 1 to 10 carbon atoms, phenyl or taken together, are alkylene of 2 to 5 carbon atoms to form a ring group.

This succinimide may be a part of a lubricating oil composition comprising a major amount of oil of lubricating viscosity and a minor amount of this succinimide. This succinimide may also be a part of a lubricating oil concentrate comprising from about 10 wt. % to about 90 wt. % of this succinimide and from about 90 wt. % to about 10 wt. % of an oil of lubricating viscosity. This succinimide may also be a part of a fuel concentrate comprising a major amount of an inert stable oleophilic organic solvent boiling in the range of about 150° F. to about 400° F. and a minor amount of this polymer. This succinimide may also be post treated with one or more cyclic carbonates or one or more linear mono- or poly-carbonates under reactive conditions to form one or more post-treated dispersants. A preferred cyclic carbonate is ethylene carbonate. This post-treated dispersant may be a part of a lubricating oil comprising a minor amount of the post-treated dispersant and a major amount of an oil of lubricating viscosity. The lubricating oil concentrate may comprise from about 10 wt. % to about 90 wt. % of this post-treated dispersant and from 90 wt. % to about 10 wt. % of an oil of lubricating viscosity. The polymer may also be post-treated with one or more of boron oxide, boron halide, boric acid, and esters of boric acid under reactive conditions to form one or more post-treated dispersants.

A process for preparing one or more succinimides comprises reacting (a) a low molecular weight branched ASAD prepared by reacting (1) one or more unsaturated acidic reagents with (2) one or more polyisobutenes which contain from about 8 to about 32 carbon atoms and wherein at least 50% of the olefinic bonds of the low molecular weight polyisobutene or the mixture of low molecular weight polyisobutenes comprise methylvinylidene isomer plus tri-substituted isomer, and (b) one or more polyamines. The acid derivative may have a succinic ratio of 1.0 or greater, and preferably from about 1.1 to about 1.4. This succinimide may be prepared by reacting a mixture under reactive conditions wherein the mixture comprises one or more low molecular weight branched ASAD of one or more unsaturated acidic reagents and one or more polyisobutenes having less than about 32 carbon atoms, and one or more polyamines. The unsaturated acidic reagent may comprise maleic anhydride. This invention may comprise a lubricating oil composition comprising a major amount of an oil of lubricating viscosity and a minor amount of this succinimide, more particularly, about 0.10 wt. % to about 10 wt. % of this succinimide. This invention may comprise one or more fuel concentrates that comprise a major amount of an inert stable oleophilic organic solvent boiling in the range of about 150° F. to about 400° F. and a minor amount of this succinimide.

This succinimide may be post-treated with one or more of the following carbonates, linear mono-carbonates and poly-carbonates, under reactive conditions. The carbonates may comprise ethylene carbonate. This invention may comprise a lubricating oil comprising a major amount of an oil of lubricating viscosity and a minor amount of this post-treated succinimide, or more particularly, about 0.10 wt. % to about 10 wt. % of this post-treated succinimide. This invention may also comprise a fuel concentrate comprising a major amount of an inert stable oleophilic organic solvent boiling in the range of about 150° F. to about 400° F. and a minor amount of this post-treated succinimide. This invention may comprise one or more post-treated succinimides prepared by treating succinimides under reactive conditions with a one or more of boron oxide, boron halide, boric acid, and esters of boric acid. The succinimides of this invention may also be post-treated with one or more boron oxide, boron halide, boric acid, and esters of boric acid. This invention may also comprise lubricating oil comprising a major amount of oil of lubricating viscosity and a minor amount of the succinimide post treated with a boron compound. This invention may comprise a fuel concentrate comprising a major amount of an inert stable oleophilic organic solvent boiling in the range of about 150° F. to about 400° F. and a minor amount of this succinimide that has been post treated with one or more boron compounds.

Definitions

As used in this patent application, whether or not capitalized, the following terms have the following meanings unless specifically stated otherwise.

The term "PIB" is an abbreviation for polyisobutene.

The terms "low molecular weight PIB" refer herein to PIBs that comprise from about 8 to about 32 carbons atoms and a number average molecular weight less than 450 and wherein polybutene contains at least 50% of the methylvinylidene isomer plus tri-substituted isomer.

The term "methylvinylidene" or "methylvinylidene isomer" refers to olefins and polyalkylene components having the following vinylidene structure

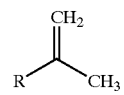

(E)

wherein R is polyisobutyl group having less than about 29 carbon atoms. The term trisubstituted isomer refers to olefins and polyalkylene components having the following trisubstituted structure

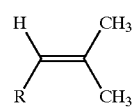

(F)

wherein R is polyisobutyl group having less than about 28 carbon atoms.

The term "succinimide" is understood in the art to include any of the amide, imide, etc. species that are also formed by the reaction of a succinic anhydride with an amine. The predominant products, however, are succinimides and this term has been generally accepted as meaning the product of a reaction of alkenyl- or alkyl-substituted succinic acid or anhydride with polyamine. Alkenyl or alkyl succinimides are disclosed in numerous references and are well known in the art. Certain fundamental types of succinimides and related materials encompassed by the term of art "succinimide" are taught in U.S. Pat. Nos. 2,992,708; 3,018,291; 3,024,237; 3,100,673; 3,219,666; 3,172,892; and 3,272,746, the disclosures of which are hereby incorporated by reference.

The term "Total Base Number" or "TBN" refers to the amount of base equivalent to milligrams of KOH in 1 gram of sample. Thus, higher TBN numbers reflect more alkaline products and therefore a greater alkalinity reserve. The TBN of a sample may be determined by ASTM Test No. D2896 or any other equivalent procedure.

The term "SAP" refers to Saponification Number and may be determined by the procedure described in ASTM Test No. D94 or any other equivalent procedure.

The term "TAN" refers to Total Acid Number and may be determined by the procedure described in ASTM Test No. D 664 or any other equivalent procedure.

The "succinic ratio" may be calculated from the saponification number (mg KOH per gram of sample), the actives content of the alkenyl or alkyl succinic anhydride product and the molecular weight of the starting polyolefin. The actives content of the alkenyl or alkyl succinic anhydride product is measured in terms of the actives fraction, wherein an actives fraction of 1.0 is equivalent to 100 weight percent actives. Accordingly, an actives fraction of 0.5 would correspond to 50 weight percent actives.

The succinic ratio of the alkenyl or alkyl succinic anhydride product of maleic anhydride and polyolefin can be calculated in accordance with the following equation:

$$\text{Succinic ratio} = \frac{M_{po} \times P}{(C \times A) - (M_{ma} \times P)}$$

wherein

P=saponification number of the alkenyl or alkyl succinic anhydride sample (mg KOH/g)

A=actives fraction of the alkenyl or alkyl succinic anhydride sample $M_{po}$=number average molecular weight of the starting polyolefin $M_{ma}$=98 (molecular weight of maleic anhydride)

C=conversion factor=112220 (for conversion of grammoles of alkenyl or alkyl succinic anhydride per gram of sample to milligrams of KOH per gram of sample).

The actives fraction of the alkenyl or alkyl succinic anhydride may be determined from the percent of unreacted polyolefin according to the following procedure. A 5.0 gram sample of the reaction product of maleic anhydride and polyolefin is dissolved in a suitable solvent, placed in a column of 80.0 grams of silica gel (Davisil 62, a 140 angstrom pore size silica gel), and eluted with 1 liter of a suitable solvent. The percent unreacted polyolefin is determined by removing the solvent under vacuum from the eluent and weighing the residue. Percent unreacted polyolefin is calculated according to the following formula:

$$PercentUnreactedPolyolefin = \frac{NetWeightofResidue}{SampleWeight} \times 100$$

The weight percent actives for the alkenyl or alkyl succinic anhydride product is calculated from the percent unreacted polyolefin using the formula:

Weight Percent Actives=100−Percent Unreacted Polyolefin

The actives fraction of the alkenyl or alkyl succinic anhydride is then calculated as follows:

$$ActivesFraction = \frac{WeightPercentActives}{100}$$

The percent conversion of polyolefin is calculated from the weight percent actives as follows:

$$PercentConversion = \frac{\text{wt. \% actives} \times \left( \frac{M_{po}}{M_{po} + [M_{ma} \times SR]} \right)}{\left[ \text{wt. \% actives} \times \left( \frac{M_{po}}{M_{po} + [M_{ma} \times SR]} \right) \right] + [100 - \text{wt. \% actives}]}$$

wherein $M_{po}$=number of average molecular weight of the starting polyolefin $M_{ma}$=98(molecular weight of maleic anhydride)

SR=succinic ratio of alkenyl or alkyl succinic anhydride product

It is, of course, understood that alkenyl or alkyl succinic anhydride products having high succinic ratios can be blended with other alkenyl succinic anhydrides having lower succinic ratios, for example ratios of around 1.0, to provide an alkenyl succinic anhydride product having an intermediate succinic ratio.

DETAILED DESCRIPTION OF THE INVENTION

A. Low Molecular Weight Branched ASAD

One embodiment of this invention is a low molecular weight branched ASAD. The low molecular weight branched ASAD may be prepared by reacting a low molecular weight PIB with an unsaturated acidic reagent thermally or optionally catalyzed in the presence of a strong acid.

Preferred low molecular weight branched ASAD include those in which an unsaturated acidic reagent, most preferably maleic anhydride, is reacted with a low molecular weight PIB wherein about 50% or more, preferably about 70% or more, and more preferably about 80% or more of the olefinic bonds of the PIB comprises methylvinylidene isomer plus tri-substituted isomer. Preferably, the methylvinylidene isomer content of the PIB will, by itself, be at least 40%, more preferably at least 50%, and even more preferably at least 60%.

Low molecular weight branched ASAD may comprise a mixture of low molecular weight PIB molecules of varying molecular weight because low molecular weight PIB used to prepare low molecular weight branched ASAD are generally mixtures of individual molecules of different molecular weights. The low molecular weight branched ASAD may have the general formula:

(A)

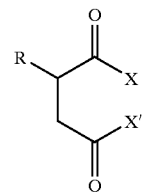

wherein X and X' are independently selected from the group consisting of: —OH; —OR$^1$, wherein R$^1$ is alkyl of 1 to 8 carbon atoms; —NH$_2$; —Cl; —Br; and —OM+, wherein M+ is equivalent of at least one of a metal, ammonium or alkyl ammonium cation wherein the alkyl group has 1 to 8 carbon atoms; and X and X' when taken together are —O— or —NH—; R is a polyisobutenyl group or a mixture of low molecular weight polyisobutenyl groups having from about 8 to about 32 carbon atoms, preferably from about 12 to about 28 carbon atoms, derived from a polyisobutene having at least 50% of the methylvinylidene isomer plus tri-substituted isomer. The low molecular weight branched ASAD may further be reacted to form may comprise one or more of an amide derivative, an ester derivative, an imide derivative and a metal salt derivative.

In a preferred embodiment, when maleic anhydride is used as the unsaturated acidic reagent, the reaction produces the following low molecular weight PIB/ASAD isomers:

(1)

(B)

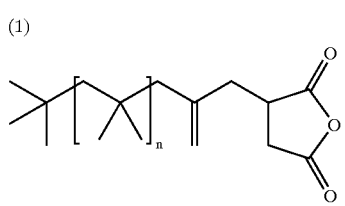

(2)

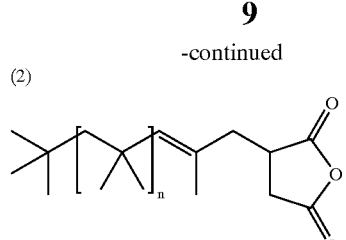

(3)

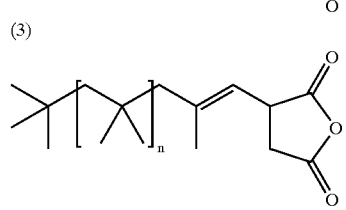

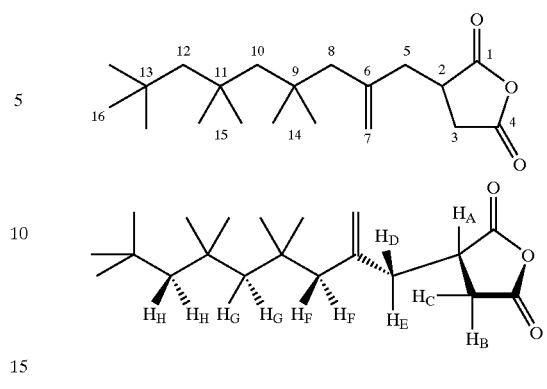

wherein n is a whole integer from 1 to 6.

The distribution of isomer (1) is from about 5% to about 60%. The distribution of isomer (2) is from about 10% to about 30%. The distribution of isomer (3) is from about 5% to about 45%.

Although isomers (1), (2) and (3) in Formula (B) are the predominate structures which are produced, other structures were also detected using NMR analysis. The isomer distribution is controlled greatly by whether an alkyl benzenesulfonic acid catalyst is employed during the reaction between the unsaturated acidic reagent and the low molecular weight PIB. Typically, if an alkyl benzenesulfonic acid catalyst is used, then the product contains a mixture of isomers (1), (2), (3) and other low molecular weight branched ASAD isomers. In the alternative, if an alkyl benzenesulfonic acid catalyst is not used, then the product contains a majority of the (1) isomer.

Characterization of the isomers (1), (2), and (3) in Figure (B) has been carried out using $^1H$ and $^{13}C$ NMR spectroscopy for the case where n=2. The $^1H$ and $^{13}C$ NMR assignment for isomer (1) is reported in Table A.

TABLE A

NMR Assignment for Isomer (1)

| Carbon Chemical Shift, ppm | Carbon Assignment | Carbon Type | Proton Chemical Shift, ppm | Proton Coupling Constants, Hz | Proton Assignment |
|---|---|---|---|---|---|
| 173.65 | C1 | C | — | — | — |
| 170.04 | C4 | C | — | — | — |
| 142.71 | C6 | C | — | — | — |
| 116.84 | C7 | $CH_2$ | 4.90 | — | Vinylidene |
| 58.02 | C12 | $CH_2$ | 1.33 | — | $H_H$ |
| 56.34 | C10 | $CH_2$ | 1.37 | — | $H_G$ |
| 50.81 | C8 | $CH_2$ | 1.98, 1.97 | — | $H_F$ |
| 39.56 | C5 | $CH_2$ | 2.80, 2.30 | $J_{DE}$ = 14.69 | $H_D$, $H_E$ |
| 39.52 | C2 | CH | 3.30 | $J_{AB}$ = 9.42, $J_{AC}$ = 5.84, $J_{AD}$ = 4.16, $J_{AE}$ = 10.59 | $H_A$ |
| 37.52 | C9 | C | — | — | — |
| 36.50 | C11 | C | — | — | — |
| 33.80 | C3 | $CH_2$ | 3.04, 2.70 | $J_{BC}$ = 19.33 | $H_B$, $H_C$ |
| 32.51 | C13 | C | — | — | — |
| 32.37 | C16 | $CH_3$ | 0.99 | — | Methyl |
| 30.58 | C15 | $CH_3$ | 1.09 | — | Methyl |
| 29.15, 28.95 | C14 | CH3 | 1.04, 1.03 | — | Methyl |

Wherein the Carbon and Hydrogen atoms are labeled in the structures below:

Likewise the NMR assignment for isomer (2) is reported in Table B.

TABLE B

NMR Assignment for Isomer (2).

| Carbon Chemical Shift, ppm | Carbon Assignment | Carbon Type | Proton Chemical Shift, ppm | Proton Coupling Constants, Hz | Proton Assignment |
|---|---|---|---|---|---|
| 173.93 | C1 | C | — | — | — |
| 170.38 | C4 | C | — | — | — |
| 140.78 | C8 | CH | 5.29 | — | Olefin |
| 126.75 | C6 | C | — | — | — |
| 57.80 | C12 | $CH_2$ | 1.29 | — | $H_H$ |
| 57.00 | C10 | $CH_2$ | 1.53 | — | $H_G$ |
| 43.34 | C5 | $CH_2$ | 2.63, 2.17 | $J_{DE}$ = 14.10 | $H_D$, $H_E$ |
| 39.24 | C2 | CH | 3.26 | $J_{AB}$ = 9.72, $J_{AC}$ = 6.03, $J_{AD}$ = 4.72, $J_{AE}$ = 10.93 | $H_A$ |
| 37.23 | C9 | C | — | — | — |
| 36.50 | C11 | C | — | — | — |
| 33.31 | C3 | $CH_2$ | 2.95, 2.70 | $J_{BC}$ = 19.10 | $H_B$, $H_C$ |
| 32.51 | C13 | C | — | — | — |
| 32.37 | C16 | $CH_3$ | — | — | — |
| 30.58 | C15 | $CH_3$ | — | — | — |
| 30.29 | C14 | $CH_3$ | — | — | — |
| 16.63 | C7 | $CH_3$ | 1.74 | — | Methyl |

Wherein the Carbon and Hydrogen are labeled in the structures below:

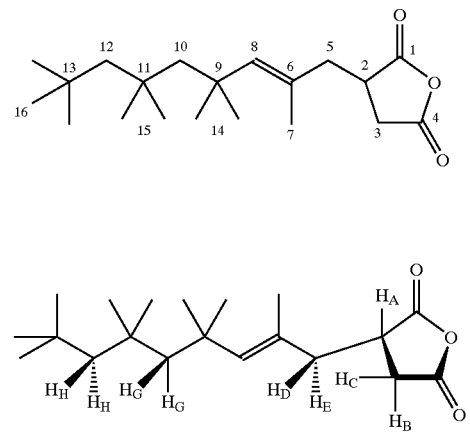

Likewise the NMR assignment for isomer (3) is reported in Table C.

TABLE C

NMR Assignment for Isomer (3).

| Carbon Chemical Shift, ppm | Carbon Assignment | Carbon Type | Proton Chemical Shift, ppm | Proton Coupling Constants, Hz | Proton Assignment |
|---|---|---|---|---|---|
| 172.38 | C1 | C | — | — | — |
| 170.11 | C4 | C | — | — | — |
| 141.98 | C6 | C | — | — | — |
| 121.38 | C5 | CH | 5.10 | — | Olefin |
| 58.02 | C12 | $CH_2$ | 1.32 | — | $H_H$ |
| 56.56 | C10 | $CH_2$ | 1.35 | — | $H_G$ |
| 54.97 | C8 | $CH_2$ | 2.06 | — | $H_F$ |
| 40.59 | C2 | CH | 4.03 | $J_{AB} = 10.17$, $J_{AC} = 5.80$, $J_{AD} = 8.30$ | $H_A$ |
| 37.50 | C9 | C | — | — | — |
| 36.50 | C11 | C | — | — | — |
| 35.74 | C3 | $CH_2$ | 3.25, 2.72 | $J_{BC} = 18.92$ | $H_B$, $H_C$ |
| 32.51 | C13 | C | — | — | — |
| 32.37 | C16 | $CH_3$ | — | — | — |
| 30.58 | C15 | $CH_3$ | — | — | — |
| 29.27 | C14 | $CH_3$ | — | — | — |
| 20.11 | C7 | $CH_3$ | 1.81 | — | Vinyl Methyl |

Wherein the Carbon and Hydrogen are labeled in the structures below:

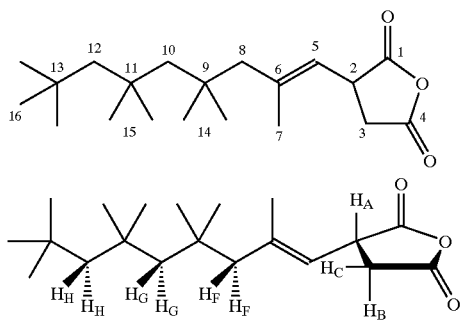

A.1. Low Molecular Weight Polyiosbutene (PIB)

The low molecular weight PIBs employed comprise from about 8 to about 32 carbon atoms, for example, one or more of 32 carbon atoms, 28 carbon atoms, 24 carbon atoms, 20 carbon atoms, 16 carbon atoms, 12 carbon atoms, and 8 carbon atoms. Preferred low molecular weight PIBs comprise from about 12 to about 32 carbon atoms. More preferred low molecular weight PIBs comprise from about 12 to about 28 carbon atoms. The low molecular weight PIBs have a number average molecular weight of about 450 or less. Preferred low molecular weight PIBs have a number average molecular weight of about 120 to about 392. More preferred low molecular weight PIBs have a number average molecular weight of about 120 to about 300.

The PIBs of this invention may be mixtures of individual low molecular weight PIB molecules of varying molecular weights. A mixture of low molecular weight PIBs might comprise any or all of $C_8$, $C_{12}$, $C_{16}$, $C_{20}$, $C_{24}$, $C_{28}$ and $C_{32}$ molecules. One embodiment of this invention may comprise the use of low molecular weight PIB molecules that have been separated according to carbon number. For example, a PIB mixture may be distilled to provide compositions that comprise one or more of $C_8$, $C_{12}$, $C_{16}$, $C_{20}$, $C_{24}$, $C_{28}$, or $C_{32}$ molecules. Preferred number average low molecular weight PIBs of this invention are those that are used as a mixture of varying molecular weights. The low molecular weight PIBs have a molecular weight of about 450 or less. Preferred low molecular weight PIBs have a molecular weight of about 120 to about 392. More preferred low molecular weight PIB has a molecular weight of about 120 to about 300.

A preferred low molecular weight PIB mixture may comprise the following: about 5 wt. % to about 20 wt. % $C_8H_{16}$, about 35 wt. % to about 55 wt. % $C_{12}H_{24}$, about 20 wt. % to about 30 wt. % $C_{16}H_{32}$, about 8 wt. % to about 15 wt. % $C_{20}H_{40}$, about 2 wt % to about 8 wt % $C_{24}H_{48}$, and about 0.5 wt % to about 2 wt % $C_{28}H_{56}$. $C_{32}H_{64}$ and higher species may comprise about 2 wt % or less of the total.

The olefinic bonds of the low molecular weight PIB comprise about 50% or more, preferably about 70% or more, and more preferably about 80% or more of the methylvinylidene isomer plus tri-substituted isomer. Preferably, the low molecular weight PIB will have a methylvinylidene isomer content of at least 40%, more preferably at least 50%, and even more preferably at least 60%

Preferred PIBs include those PIBs prepared using a boron triflouride ($BF_3$) catalyst. The preparation of PIBs in which the methylvinylidene isomer comprises a high percentage of the total composition is described in U.S. Pat. Nos. 4,152,499 and 4,605,808. Low molecular weight PIB may be prepared directly or they may be a distilled fraction of higher molecular weight polybutene.

A.2. Unsaturated Acidic Reagent

The term "unsaturated acidic reagent" refers to maleic or fumaric reagents of the general formula:

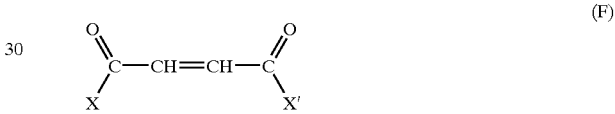

(F)

wherein X and X' are the same or different, provided that at least one of X and X' is a group that is capable of reacting to esterify alcohols, form amides, or amine salts with ammonia or amines, form metal salts with reactive metals or basically reacting metal compounds and otherwise function as acylating agents. Typically, X and X' comprise functional groups that may comprise one or more of —OH; —OR$^1$, wherein R$^1$ is an alkyl of 1 to 8 carbon atoms; —OM+ when M+ represents one equivalent of a metal, ammonium, or amine cation; —NH$_2$; —Cl; —Br; or taken together X and X' may be —O— so as to form an anhydride or may be —NH— to form a succinimide. Preferably, X and X' are such that both carboxylic functions can enter into acylation reactions. Maleic anhydride is a preferred unsaturated acidic reagent. Other suitable unsaturated acidic reagents include electron-deficient olefins such as monophenyl maleic anhydride; monomethyl, dimethyl, monochloro, monobromo, monofluoro, dichloro and difluoro maleic anhydride, N-phenyl maleimide and other substituted maleimides; isomaleimides; fumaric acid, maleic acid, alkyl hydrogen maleates and fumarates, dialkyl fumarates and maleates, fumaronilic acids and maleanic acids; and maleonitrile, and fumaronitrile.

A.3. The Strong Acid

The term "strong acid" refers to an acid having a $pK_a$ of less than about 4. Preferably, the strong acid is an oil-soluble, strong organic acid, but even inorganic strong acids would work (e.g. HCl, $H_2SO_4$, $HNO_3$, HF, etc.). More preferably, the strong acid is an alkyl aryl sulfonic acid. Still more preferably, the alkyl group of said alkyl aryl sulfonic acid has from 4 to 30 carbon atoms. Even more preferred is an alkyl benzenesulfonic acid in which the alkyl group contains 12 carbons. The use of a strong acid, such as an alkyl aryl sulfonic acid, in the preparation of a polyalkenyl derivative of an unsaturated acidic reagent is disclosed in Harrison et al., U.S. Pat. No. 6,156,850, the disclosure of which is incorporated herein by reference.

Preferably, the sulfonic acid is present in an amount in the range of from 0.0025% to 1% based on the total weight of polyalkene.

A.4. General Preparation of Low Molecular Weight Branched ASAD

The low molecular weight branched ASAD may be prepared by reacting a low molecular weight PIB with an unsaturated acidic reagent thermally or optionally in the presence of a strong acid.

The reaction may be conducted neat, that is, the low molecular weight PIB and the unsaturated acidic reagent are combined in the proper ratio, and then stirred at the reaction temperature.

The reaction time is usually sufficient to result in the substantially complete conversion of the reactive isomers of the low molecular weight PIB to the low molecular weight branched ASAD. Suitable reaction times may be between one and 24 hours, with preferred reaction times between two and ten hours.

The low molecular weight PIB, and the unsaturated acidic reagent, may be brought together in any suitable manner. No solvent is required. The important factors are intimate contact of the low molecular weight PIB and unsaturated acidic reagent. The reaction, for example, may be conducted in a batch system in which all the low molecular weight PIB is added initially to a mixture of unsaturated acidic reagent. The low molecular weight PIB may also be added intermittently or continuously to the other reactants. The components in the reaction mixture may also be added continuously to a stirred reactor with continuous removal of a portion of the product to a recovery train or to other reactors in series. The reaction may also take place in a tubular reactor in which the components may be added at one or more points along the tube.

The reaction may be conducted at a temperature of about 120° C. to about 240° C., preferably from about 180° C. to about 230° C.

The reaction may be conducted at any pressure suitable to the boiling point of the low molecular weight polyisobutene. Typically the reaction is carried out at atmospheric pressure but higher pressures may be used. Typically higher pressures are used to prevent the low molecular weight polybutene or maleic anhydride from being removed from the reaction zone through distillation.

This process may be conducted in batch or in continuous mode. The unsaturated acidic reagent charge may theoretically range from 0.5 to 2 moles of unsaturated acidic reagent per mole of methyl vinylidene isomer of PIB. More preferably the unsaturated acidic reagent charge ranges from 0.9 to 1.1. When the charge mole ratio is greater, a product may be formed that contains 2 anhydrides per PIB chain, especially wherein the succinic ratio is greater than 1. The reaction may be carried out at atmospheric pressure. At higher temperatures, it may be desirable to pressurize the reactor slightly (i.e., 10 psig) to suppress the loss of unsaturated acidic reagent to the vapor phase.

If the reaction is batch, the reactor may be stirred and heated to the desired reaction temperature, and the unsaturated acidic reagent may be added at the appropriate time/times during this step. Reaction times will vary based upon reaction temperature, concentration of reactants, use of the strong acid and concentration of the strong acid. When the reaction is complete, removal of any unreacted unsaturated acidic reagent and unreacted olefin may be accomplished by increasing the reactor temperature from about 150° C. to about 250° C., preferably from about 180° C. to about 200° C., while applying sufficient vacuum.

If the reaction is run continuously, a continuous stirred tank reactor (CSTR) or series of such reactors may be used. PIB and unsaturated acidic reagent may be fed continuously at appropriate rates so as to maintain a certain level of conversion of the reactants to PIB low molecular weight branched ASA. It is envisioned that the product stream from the reactor then is heated to a temperature in the range of about 150° C. to about 250° C. and preferably in the range from about 180° C. to about 200° C. to strip off any unreacted unsaturated acidic reagent. Vacuum may also be used to facilitate removing any unreacted unsaturated acidic reagent. It is envisioned that a wiped film evaporator or similar types of equipment may be suitable for this type of operation.

Using a diluent or a solvent is not necessary to prepare the low molecular weight branched ASAD but one may be used if desired. When a diluent is employed, those diluents that are inert to the reactants and products formed are preferred. When a solvent is employed, solvents that are inert to the reactants and products formed are preferred. Solvents may be removed after their usefulness is no longer required. The low molecular weight branched ASAD product may be conveniently separated from any solvent used and any unreacted acidic reagent by conventional procedures such as phase separation, solvent distillation, precipitation and the like. Though not required, dispersing agents and/or co-solvents may be used during the reaction if desired.

Optionally, the described preparation of low molecular weight branched ASAD may be done in the presence of a strong acid. When a strong acid is employed in the preparation of the low molecular weight ASAD of this invention, the low molecular weight PIB is reacted with the unsaturated acidic reagent in the presence of about 0.0025% to about 1.0% of the strong acid based on the total weight of PIB. The PIB preferably will contain at least 50% of the methylvinylidene plus trisubstituted isomer, more preferably at least 70% of the methylvinylidene plus trisubstituted isomer, and most preferably at least about 80% of the methylvinylidene plus trisubstituted isomer. Preferably, the PIB will also contain at least 40% of the methylvinylidene isomer, more preferably at least 60% of the methylvinylidene isomer, and even more preferably at least 70% of the methylvinylidene isomer.

B. Succinimides

One embodiment of this invention is a succinimide that may be referred to herein as a low molecular weight branched ASAD succinimide. This succinimide may be depicted as the general formula:

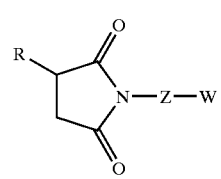

(C)

wherein:

W comprises one or more of:

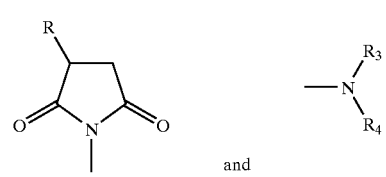

(D)

and wherein R is a polyisobutenyl group having from about 8 to about 32 carbon atoms, preferably about 12 to 28 carbon atoms, or a mixture of low molecular weight polyisobutenyl groups having from about 8 to about 32 carbon atoms, preferably about 12 to 28 carbon atoms, derived from a PIB having greater than 50% methylvinylidene isomer plus methylvinylidene tri-substituted isomer; Z is one or more polyamine linking radicals; and wherein $R_3$ and $R_4$ are independently hydrogen, alkyl of 1 to 10 carbon atoms, phenyl or taken together, are alkylene of 2 to 5 carbon atoms to form a ring group.

The compound of formula (C) may be considered a low molecular weight branched ASAD succinimide and is produced by the reaction of a low molecular weight branched ASAD with a polyamine. Because the low molecular weight branched ASAD succinimide mixture may contain about from 0.4 to 1.0 equivalents of polyamine per equivalent of low molecular weight branched ASAD, other structures may be present.

In addition to the predominant succinimide of formula (C) the reaction will typically contain more complex reaction products and structures because of competing and sequential reactions.

Referring to formula (C), the preferred compounds or compound mixtures are those wherein R is a low molecular weight PIB, and wherein Z is a polyamino radical having about from 3 to 7, more preferably, about 4 to 5 nitrogen atoms and 8 to 20 carbon atoms.

B.1. Synthesis of Low Molecular Weight PIB Succinimide

A succinimide composition comprising low molecular weight branched ASAD succinimides may be prepared by contacting the desired low molecular weight branched ASAD with a polyamine under reactive conditions. Typically, the reaction is conducted at temperatures in the range of from about 140° C. to about 180° C., preferably from about 150° C. to about 170° C. for from about 1 to about 10 hours, preferably from about 4 to about 6 hours. Typically, the reaction is conducted at about atmospheric pressure; however, higher or lower pressures can also be used depending on the reaction temperature desired and the boiling point of the reactants or solvent if a solvent is used.

As noted herein, the reaction will typically be a mixture because there are secondary products or byproducts and the reactants are mixtures. In theory, pure compounds could be obtained, for example by using pure compounds as reactants and then separating out the desired pure compounds from the reaction product. However, the expense of this would rarely be justified for commercial purposes and accordingly the commercial product will generally be a mixture.

Water, present in the system or generated by the reaction of the amine with the low molecular weight branched ASAD, is preferably removed from the reaction system during the course of the reaction via azeotroping, stripping with nitrogen or distillation. After reaction completion, the system may be stripped at elevated temperatures (typically 100° C. to 250° C.) and reduced pressures to remove any volatile components that may be present in the product.

B.2. The Polyamine Reactant

The polyamine reactant should have at least three amine nitrogen atoms per molecule, and preferably 4 to 12 amine nitrogens per molecule. Most preferred are polyamines having from about 6 to about 10 nitrogen atoms per molecule. The number of amine nitrogen atoms per molecule of polyamine is calculated as follows:

$$\text{Average number of nitrogen atoms in molecule of polyamine} = \frac{\% N \times M_{pa}}{14 \times 100}$$

wherein % N=percent nitrogen in polyamine or polyamine mixture $M_{pa}$=number average molecular weight of the polyamine or polyamine mixture Preferred polyalkylene polyamines comprise from about 4 to about 20 carbon atoms, there being preferably from 2 to 3 carbon atoms per alkylene unit. The polyamine preferably has a carbon-to-nitrogen ratio of from about 1:1 to about 10:1. Examples of suitable polyamines that may be used to form the compounds of this invention include the following: Tetraethylene pentamine (TEPA), pentaethylene hexamine, Dow E-100® heavy polyamine (number=303, available from Dow Chemical Company, Midland, Mich.), and Union Carbide HPA-X heavy polyamine (number average molecular weight=275, available from Union Carbide Corporation, Danbury, Conn.). Such amines encompass isomers, such as branched-chain polyamines, and the previously mentioned substituted polyamines, including hydrocarbyl-substituted polyamines. HPA-X heavy polyamine ("HPA-X") contains an average of approximately 6.5 amine nitrogen atoms per molecule. Such heavy polyamines generally afford excellent results.

The polyamine reactant may be a single compound but typically will be a mixture of compounds reflecting commercial polyamines. The commercial polyamine will typically be a mixture in which one or several compounds predominate with the average composition indicated. For example, TEPA prepared by the polymerization of aziridine or the reaction of dichloroethylene and ammonia will have both lower and higher amine members, e.g., TEPA, substituted piperazines and pentaethylene hexamine, but the composition will be largely TEPA and the empirical formula of the total amine composition will closely approximate that of TEPA.

Other examples of suitable polyamines include admixtures of amines of various sizes, provided that the overall mixture contains at least 4 nitrogen atoms per molecule. Included within these suitable polyamines are mixtures of diethylene triamine ("DETA") and heavy polyamine. A preferred polyamine admixture reactant is a mixture containing 20% by weight DETA and 80% by weight HPA-X; as determined by the method described herein, this preferred polyamine reactant contains an average of about 5.2 nitrogen atoms per mole.

Methods of preparing polyamines and their reactions are detailed in Sidgewick's THE ORGANIC CHEMISTRY OF NITROGEN, Clarendon Press, Oxford, 1966; Noller's CHEMISTRY OF ORGANIC COMPOUNDS, Saunders, Philadelphia, 2nd Ed., 1957; and Kirk-Othmer's ENCYCLOPEDIA OF CHEMICAL TECHNOLOGY, 2nd Ed., especially Volumes 2, pp. 99–116.

C. Post-Treatments

The ASAD succinimide prepared using the low molecular weight branched ASAD may be post-treated with a wide variety of post-treating reagents. U.S. Pat. No. 4,234,435, the disclosure of which is incorporated herein by reference, discloses reacting succinic acylating agents with a variety of reagents to give post-treated carboxylic acid derivative compositions that are useful as polysuccinimides and detergents in lubricating oil compositions. For example, the dispersancy of the ASAD succinimide prepared using the low molecular weight branched ASAD may be improved by reaction with a cyclic carbonate. This may result in some reduction in fluorocarbon elastomer compatibility. However, this may generally be more than offset by reducing the concentration of the carbonated post-treated polymer in light of the increased dispersancy. The resulting modified polymer has one or more nitrogens of the polyamino moiety substituted with a hydroxy hydrocarbyl oxycarbonyl, a hydroxy poly(oxyalkylene) oxycarbonyl, a hydroxyalkylene, hydroxyalkylenepoly(oxyalkylene), or mixture thereof.

The cyclic carbonate post-treatment may be conducted under conditions sufficient to cause reaction of the cyclic carbonate with secondary amino group of the polyamino substituents. Typically, the reaction is conducted at temperatures of about from about 0° C. to about 250° C., preferably from about 100° C. to about 200° C. and most preferred from about 50° C. to about 180° C.

The reaction may be conducted neat, wherein both the polymer and the cyclic carbonate are combined in the proper ratio, either alone or in the presence of a catalyst (such as an acidic, basic or Lewis acid catalyst). Examples of suitable catalysts include, for example, phosphoric acid, boron trifluoride, alkyl or aryl sulfonic acid, alkali or alkaline carbonate. The same solvents or diluents as described herein with respect to the preparing the ASAD succinimde may also be used in the cyclic carbonate post-treatment.

The reaction of polyamino alkenyl or alkyl succinimides with cyclic carbonates is known in the art and is described in U.S. Pat. No. 4,612,132, hereby incorporated by reference, in its entirety. Generally, the procedures described to post-treat polyamino alkenyl or alkyl succinimides with cyclic carbonates may also be applied to post treat the ASAD succinimide.

A particularly preferred cyclic carbonate may be 1,3-dioxolan-2-one (ethylene carbonate).

The molar charge of cyclic carbonate employed in the post-treatment reaction is preferably based upon the theoretical number of basic nitrogens contained in the polyamino substituent of the succinimide. Thus, when one equivalent of tetraethylene pentamine (TEPA) is reacted with one equivalent of succinic anhydride and one equivalent of the low molecular weight PIB/UAR, the resulting bis succinimide will theoretically contain 3 basic nitrogens. Accordingly, a molar charge of 2 would require that two moles of cyclic carbonate be added for each basic nitrogen or in this case 6 moles of cyclic carbonate for each mole equivalent of polyalkylene succinimide or succinimide prepared from TEPA. Mole ratios of the cyclic carbonate to the basic amine nitrogen of the polyamino alkenyl succinimide used in the process of this invention are typically in the range of from about 1:1 to about 4:1, although preferably from about 2:1 to about 3:1.

As described in U.S. Pat. No. 4,612,132, cyclic carbonates may react with the primary and secondary amines of a polyamino alkenyl or alkyl succinimide to form two types of compounds. First, strong bases including unhindered amines such as primary amines and some secondary amines, react with an equivalent of cyclic carbonate to produce a carbamic ester. Second, hindered bases, such as hindered secondary amines, may react with an equivalent of the same cyclic carbonate to form a hydroxyalkyleneamine linkage. (Unlike the carbamate products, the hydroxyalkyleneamine products retain their basicity.) Accordingly, the reaction of a cyclic carbonate may yield a mixture of products. When the molar charge of the cyclic carbonate to the basic nitrogen of the succinimide is about 1 or less, a large portion of the primary and secondary amines of the succinimide will be converted to hydroxy hydrocarbyl carbamic esters with some hydroxy-hydrocarbylamine derivatives also being formed. As the mole ratio is raised above about 1, increased amounts of poly(oxyalkylene) polymers of the carbamic esters and the hydroxyhydrocarbylamine-derivatives may be produced.

The ASAD succinimde prepared using the low molecular weight branched ASAD and the post-treated ASAD succinimide prepared using the low molecular weight branched ASAD may also be reacted with boric acid or a similar boron compound to form borated dispersants having utility within the scope of this invention. In addition to boric acid (boron acid), examples of suitable boron compounds include boron oxides, boron halides and esters of boric acid. Generally from about 0.1 equivalents to about 10 equivalents of boron compound to succinimide may be used.

In addition to the carbonate and boric acid post-treatments, the compounds may be post-treated, or further post-treatment, with a variety of post-treatments designed to improve or impart different properties. Such post-treatments include those summarized in columns 27–29 of U.S. Pat. No. 5,241,003, hereby incorporated by reference. Such treatments may include treatment with:

Inorganic phosphorous acids or anhydrates (e.g., U.S. Pat. Nos. 3,403,102 and 4,648,980);

Organic phosphorous compounds (e.g., U.S. Pat. No. 3,502,677);

Phosphorous pentasulfides;

Boron compounds as already noted herein (e.g., U.S. Pat. Nos. 3,178,663 and 4,652,387);

Carboxylic acid, polycarboxylic acids, anhydrides and/or acid halides (e.g., U.S. Pat. Nos. 3,708,522 and 4,948,386);

Epoxides polyepoxiates or thioexpoxides (e.g., U.S. Pat. Nos. 3,859,318 and 5,026,495);

Aldehyde or ketone (e.g., U.S. Pat. No. 3,458,530);

Carbon disulfide (e.g., U.S. Pat. No. 3,256,185);

Glycidol (e.g., U.S. Pat. No. 4,617,137);

Urea, thourea or guanidine (e.g., U.S. Pat. Nos. 3,312,619; 3,865,813; and British Patent GB 1,065,595);

Organic sulfonic acid (e.g., U.S. Pat. No. 3,189,544 and British Patent GB 2,140,811);

Alkenyl cyanide (e.g., U.S. Pat. Nos. 3,278,550 and 3,366,569);

Diketene (e.g., U.S. Pat. No. 3,546,243);

A diisocyanate (e.g., U.S. Pat. No. 3,573,205);

Alkane sultone (e.g., U.S. Pat. No. 3,749,695);

1,3-Dicarbonyl Compound (e.g., U.S. Pat. No. 4,579,675);

Sulfate of alkoxylated alcohol or phenol (e.g., U.S. Pat. No. 3,954,639);

Cyclic lactone (e.g., U.S. Pat. Nos. 4,617,138; 4,645,515; 4,668,246; 4,963,275; and 4,971,711);

Cyclic carbonate or thiocarbonate linear monocarbonate or polycarbonate, or chloroformate (e.g., U.S. Pat. Nos. 4,612,132; 4,647,390; 4,648,886; 4,670,170);

Nitrogen-containing carboxylic acid (e.g., U.S. Pat. No. 4,971,598 and British Patent GB 2,140,811);

Hydroxy-protected chlorodicarbonyloxy compound (e.g., U.S. Pat. No. 4,614,522);

Lactam, thiolactam, thiolactone or ditholactone (e.g., U.S. Pat. Nos. 4,614,603 and 4,666,460);

Cyclic carbonate or thiocarbonate, linear monocarbonate or plycarbonate, or chloroformate (e.g., U.S. Pat. Nos. 4,612,132; 4,647,390; 4,646,860; and 4,670,170);

Nitrogen-containing carboxylic acid (e.g., U.S. Pat. No. 4,971,598 and British Patent GB 2,440,811);

Hydroxy-protected chlorodicarbonyloxy compound (e.g., U.S. Pat. No. 4,614,522);

Lactam, thiolactam, thiolactone or dithiolactone (e.g., U.S. Pat. No. 4,614,603, and 4,666,460);

Cyclic carbamate, cyclic thiocarbamate or cyclic dithiocarbamate (e.g., U.S. Pat. Nos. 4,663,062 and 4,666,459);

Hydroxyaliphatic carboxylic acid (e.g., U.S. Pat. Nos. 4,482,464; 4,521,318; 4,713,189);

Oxidizing agent (e.g., U.S. Pat. No. 4,379,064);

Combination of phosphorus pentasulfide and a polyalkylene polyamine (e.g., U.S. Pat. No. 3,185,647);

Combination of carboxylic acid or an aldehyde or ketone and sulfur or sulfur chloride (e.g., U.S. Pat. Nos. 3,390,086; 3,470,098);

Combination of a hydrazine and carbon disulfide (e.g. U.S. Pat. No. 3,519,564);

Combination of an aldehyde and a phenol (e.g., U.S. Pat. Nos. 3,649,229; 5,030,249; 5,039,307);

Combination of an aldehyde and an O-diester of dithiophosphoric acid (e.g., U.S. Pat. No. 3,865,740);

Combination of a hydroxyaliphatic carboxylic acid and a boric acid (e.g., U.S. Pat. No. 4,554,086);

Combination of a hydroxyaliphatic carboxylic acid, then formaldehyde and a phenol (e.g., U.S. Pat. No. 4,636,322);

Combination of a hydroxyaliphatic carboxylic acid and then an aliphatic dicarboxylic acid (e.g., U.S. Pat. No. 4,663,064);

Combination of formaldehyde and a phenol and then glycolic acid (e.g., U.S. Pat. No. 4,699,724);

Combination of a hydroxyaliphatic carboxylic acid or oxalic acid and then a diisocyanate (e.g. U.S. Pat. No. 4,713,191);

Combination of inorganic acid or anhydride of phosphorus or a partial or total sulfur analog thereof and a boron compound (e.g., U.S. Pat. No. 4,857,214);

Combination of an organic diacid then an unsaturated fatty acid and then a nitrosoaromatic amine optionally followed by a boron compound and then a glycolating agent (e.g., U.S. Pat. No. 4,973,412);

Combination of an aldehyde and a triazole (e.g., U.S. Pat. No. 4,963,278);

Combination of an aldehyde and a triazole then a boron compound (e.g., U.S. Pat. No. 4,981,492);

Combination of cyclic lactone and a boron compound (e.g., U.S. Pat. No. 4,963,275 and 4,971,711).

D. Lubricating Oil Compositions

The low molecular weight branched ASAD and ASAD succinimides made using the low molecular weight branched ASAD and post-treated ASAD succinimides made using the low molecular weight branched ASAD all of which are described herein are useful as detergent and dispersant additives when used in lubricating oils. When used as detergents or dispersants, these additives may be used at about 0.1 to about 10 wt. % of the total lubricating oil composition and preferably at about 0.5 wt. % to about 8 wt. % and more preferably at about 1 wt. % to about 6 wt. % of the total lubricating oil composition.

The lubricating oil used with these additive compositions may be mineral oil or synthetic oils of lubricating viscosity and preferably suitable for use in the crankcase of an internal combustion engine. Crankcase lubricating oils ordinarily have a viscosity of about 1300 cSt at 0° F. (−18° C.) to 22.7 cSt at 210° F. (99° C.). The lubricating oils may be derived from synthetic or natural sources. Hydrocarbon synthetic oils may include, for example, oils prepared from the polymerization of ethylene, i.e., polyalphaolefin or PAO, or from hydrocarbon synthesis procedures using carbon monoxide and hydrogen gases such as in a Fisher-Tropsch process. Mineral oil for use as the base oil in this invention may include paraffinic, naphthenic and other oils that are ordinarily used in lubricating oil compositions. Synthetic oils include both hydrocarbon synthetic oils and synthetic esters. Useful synthetic hydrocarbon oils include liquid polymers of alpha olefins having the proper viscosity. The hydrogenated liquid oligomers of $C_6$ to $C_{12}$ alpha olefins such as 1-decene trimer are especially useful. Alkyl benzenes of proper viscosity, such as didodecyl benzene may also be used.

Hydrocarbon oils blended with synthetic oils may also be useful. For example, blends of 10 to 25 wt. % hydrogenated 1-decene trimer with 75 to 90 wt. % 150 SUS (100° F.) mineral oil are preferred as a lubricating oil base.

Lubricating oil concentrates are also envisioned. These concentrates usually include from about 90 wt. % to about 10 wt. %, preferably from about 90 wt. % to about 50 wt. %, of an oil of lubricating viscosity and from about 10 wt. % to about 90 wt. %, preferably from about 10 wt. % to about 50 wt. %, of the additives described herein. Typically, the concentrates contain sufficient diluent to make them easy to handle during shipping and storage. Suitable diluents for the concentrates include any inert diluent, preferably an oil of lubricating viscosity, so that the concentrate may be readily mixed with lubricating oils to prepare lubricating oil compositions. Suitable lubricating oils that may be used as diluents typically have viscosity in the range from about 35 to about 500 Saybolt Universal Seconds (SUS) at 100° F. (38° C.), although any oil of lubricating viscosity may be used.

Other additives that may be used include rust inhibitors, foam inhibitors, corrosion inhibitors, metal deactivators, pour point depressants, antioxidants, and a variety of other well-known additives.

It is also contemplated that the additives described herein may be employed as dispersants and detergents in hydraulic fluids, marine crankcase lubricants and the like. When so employed, the additive is added at from about 0.1 to about 10% by weight to the oil, and preferably, from about 0.5 to about 8 wt. %.

E. Fuel Compositions

The ASADs of the present invention and derivatives thereof may also be employed as additives for hydrocarbon fuels. The proper concentration of the additive described herein that are necessary to achieve the desired detergency in fuel compositions is dependent upon a variety of factors including the type of fuel used, the presence of other detergents or dispersants or other additives, etc. Generally, however, the range of additive concentration in the base fuel is 10 to 10,000 weight parts per million, preferably from 30 to 5000 parts per million of the additive per part of base fuel. If other detergents are present, a lesser amount of the additive may be used. The additives described herein may be formulated as a fuel concentrate, using an inert stable oleophilic organic solvent boiling in the range of about 150° F. to about 400° F. An aliphatic or an aromatic hydrocarbon solvent is preferred. Preferred solvents include benzene, toluene, xylene or higher-boiling aromatics or aromatic thinners. Aliphatic alcohols of about 3 to 8 carbon atoms, such as isopropanol, isobutylcarbinol, n-butanol and the like, in combination with hydrocarbon solvents are also suitable for use with the fuel additive. In the fuel concentrate, the amount of the additive will ordinarily be about 5 or more wt. % and generally not exceed about 70 wt. %, preferably from about 5 wt. % to about 50 wt. and more preferably from about 10 wt. % to about 25 wt. %.

F. Surface Sizing Agents

It is has also been discovered that the low molecular weight branched ASAD described herein may be used as is or as an intermediate for surface sizing agents for paper products. Typically the ASAD is applied (i.e. either to the surface of the paper, or other similar substrate, or in the pulp mixture) in such a way that a drop of water on the cellulose surface has an initial contact angle greater than 90° and less than 101°. Applying the ASAD allows for limited wetting and prevents the liquid from penetrating the surface of the paper product.

G. Pour Point Depressants

It is also contemplated that the low molecular weight branched ASAD described herein may be used as is or as an intermediate for pour point depressants.

H. Transmission Fluids

The low molecular weight branched ASAD succinimides made using the low molecular weight branched ASAD, and post-treated ASAD succinimides made using the low molecular weight branched ASAD all of which are described herein are useful as friction modification additives when used in automatic or continuously variable transmission (CVT) fluids. These additives may be used at about 0.1 to about 10 wt. % of the total oil composition and preferably at about 0.5 wt. % to about 8 wt. % and more preferably at about 1 wt. % to about 6 wt. % of the total transmission fluid (oil) composition. These low molecular weight branched ASAD, succinimides made using the low molecular weight branched ASAD and post-treated ASAD succinimides made using the low molecular weight branched ASAD are particularly useful in automatic transmission fluids to provide torque capacity and to mediate stick-slip during transmission lock up (shudder).

The lubricating oil used with these additive compositions may be mineral oil or synthetic oils of lubricating viscosity and preferably suitable for use in an automatic transmission or CVT. Typical automatic transmission fluids oils have a viscosity of about 20 cSt at 40° C. to 7.5 cSt at 100° C., and 16000 cP at −40° C. to 1000 cP at −20° C. The transmission fluids oils may be derived from synthetic or natural sources. Hydrocarbon synthetic oils may include, for example, oils prepared from the polymerization of ethylene, i.e., polyalphaolefin or PAO, or from hydrocarbon synthesis procedures using carbon monoxide and hydrogen gases such as in a Fisher-Tropsch process. Mineral oil for use as the base oil in this invention may include paraffinic, naphthenic and other oils that are ordinarily used in lubricating oil compositions. Synthetic oils include both hydrocarbon synthetic oils and synthetic esters. Useful synthetic hydrocarbon oils include liquid polymers of alpha olefins having the proper viscosity. The hydrogenated liquid oligomers of $C_6$ to $C_{12}$ alpha olefins such as 1-decene trimer are especially useful. Alkyl benzenes of proper viscosity, such as didodecyl benzene may also be used.

Hydrocarbon oils blended with synthetic oils may also be useful. For example, blends of 10 to 25 wt. % hydrogenated 1-decene trimer with 75 to 90 wt. % 150 SUS (100° F.) mineral oil are preferred as a lubricating oil base.

Transmission fluid additive packages (concentrates) are also envisioned. These concentrates usually include from about 90 wt. % to about 10 wt. %, preferably from about 90 wt. % to about 50 wt. %, of an oil of lubricating viscosity and from about 10 wt. % to about 90 wt. %, preferably from about 10 wt. % to about 50 wt. %, of the additives described herein. Typically, the concentrates contain sufficient diluent to make them easy to handle during shipping and storage. Suitable diluents for the concentrates include any inert diluent, preferably an oil of lubricating viscosity, so that the concentrate may be readily mixed with lubricating oils to prepare lubricating oil compositions. Suitable lubricating oils that may be used as diluents typically have viscosity in the range from about 35 to about 500 Saybolt Universal Seconds (SUS) at 100° F. (38° C.), although any oil of lubricating viscosity may be used.

Other additives that may be used include rust inhibitors, foam inhibitors, corrosion inhibitors, metal deactivators, pour point depressants, antioxidants, and a variety of other well-known additives.

It is also contemplated that the alkenyl succinic acid derivative described herein may be employed as friction modifiers for tractor hydraulic fluids, other power transmission fluids and the like. When so employed, the additive is added at from about 0.1 to 10% by weight to the oil, and preferably, from about 0.5 to 8 wt. %.

The following examples are included to demonstrate preferred embodiments of the invention. It should be appreciated by those of skill in the art that the techniques disclosed in the examples that follow may represent techniques discovered by the inventor to function well in the practice of the invention, and thus may be considered to constitute preferred modes for its practice. However, those of skill in the art should, in light of the present disclosure, appreciate that many changes may be made in the specific embodiments that are disclosed and still obtain a like or similar result without departing from the spirit and scope of the invention.

EXAMPLE 1

Preparation of Low Molecular Weight Branched ASAD

Low molecular weight PIB ($C_{20}$–$C_{28}$ distillation cut) with a number average molecular weight of 308.7 (75.10 g, 0.243 mol), and a methylvinylidene isomer content of 73.1% and a tri-substituted isomer content of 11%, was reacted with maleic anhydride, 21.46 g, 0.218 mol at 200° C. for 4 hours. The maleic anhydride was added in portions at 180° C. via a solid addition funnel. The maleic anhydride/low molecular weight PIB charge mole ratio (CMR) was 0.90. The mixture turned brown in color. The unreacted maleic anhydride was then removed by distillation under water aspirator vacuum. A total of 73.07 g of liquid product was obtained that had a saponification number of 201.4 mg/KOH/g sample. A summary of the conditions used for this preparation is shown in Table 1.

EXAMPLES 2–9

A number of additional reactions of low molecular weight PIB and maleic anhydride were carried out using the procedure in example 1. In some cases unreacted PIB was removed by vacuum distillation. Also in some cases a resin inhibitor was also added. For example in examples 3–7, 0.05 g boric acid was added to the reaction mixture before heating. In examples 8 and 9, 0.1 g of an alkylbenzene sulfonic acid was added to the reaction mixture before heating. A summary of the conditions used for these preparations is shown in Table 1.

TABLE I

Reaction Conditions Using Low Molecular Weight PIB with Greater Than 50% Methylvinylidene Isomer and Tri-substituted Isomer Content

| Ex. | PIB | # mol | CMR | other | Time, (hr) | Temp, (° C.) | Wt prod | Wt ovhd | Wt residue | physical state | % $MV^a$ | % $TSI^b$ |
|---|---|---|---|---|---|---|---|---|---|---|---|---|
| 1 | $C_{20-28}$ | 0.243 | 0.9 | — | 4 | 200 | 73.07 | — | — | liquid | 73.1 | 11 |
| 2 | $C_{16}$ | 0.326 | 0.9 | — | 4 | 200 | 86.49 | — | — | liquid | 58.0 | 10.7 |
| 3 | $C_{20-28}$ | 0.225 | 0.67 | Boric acid | 4 | 200 | — | 18.23 | 52.75 | liquid | 73.1 | 11 |

TABLE I-continued

Reaction Conditions Using Low Molecular Weight PIB with Greater Than 50% Methylvinylidene Isomer and Tri-substituted Isomer Content

| Ex. | PIB | # mol | CMR | other | Time, (hr) | Temp, (° C.) | Wt prod | Wt ovhd | Wt residue | physical state | % MV[a] | % TSI[b] |
|---|---|---|---|---|---|---|---|---|---|---|---|---|
| 4 | $C_{16}$ | 0.30 | 0.67 | Boric acid | 4 | 200 | — | 30.75 | 31.62 | liquid | 58.0 | 10.7 |
| 5 | $C_{16}$ | 0.30 | 0.67 | Boric acid | 14 | 180 | — | 8.34 | 55.0 | liquid | 58.0 | 10.7 |
| 6 | $C_{16}$ | 0.30 | 0.67 | Boric acid | 14 | 160 | — | 5.55 | 71.93 | liquid | 58.0 | 10.7 |
| 7 | $C_{16}$ | 0.30 | 0.67 | Boric acid | 14 | 140 | — | 8.16 | 58.6 | liquid | 58.0 | 10.7 |
| 8 | $C_{16}$ | 0.30 | 0.67 | Sulf. acid | 14 | 140 | — | 2.43 | 77.72 | liquid | 58.0 | 10.7 |
| 9 | $C_{16}$ | 0.30 | 0.67 | Sulf. acid | 14 | 140 | — | 5.81 | 70.49 | liquid | 58.0 | 10.7 |

[a]MV = methylvinylidene isomer
[b]TSI = tri-substituted isomer

Comparative Example A

Tetradecene 19.64 g, 0.1 mol was reacted with maleic anhydride 9.31 g, 0.0.095 mol at 190° C. for 4 hours. The maleic anhydride/low molecular weight PIB CMR was 0.95. The mixture turned brown in color. The unreacted maleic anhydride was then removed by distillation under water aspirator vacuum. A solid product was obtained. A summary of the conditions used for this preparation is shown in Table 2.

Comparative Examples B–H

A number of other reaction using different times and conditions were also carried out. In some cases the unreacted olefin was removed by vacuum distillation. Also, in some cases a resin inhibitor was also added. For example in Examples E and H 0.05 g boric acid was added before heating. In example B 0.5 g of an alkylbenzene sulfonic acid was added before heating. And in Example G 0.22 g hydroquinone was added before heating. These examples are also summarized in Table 2.

TABLE 2

Reaction Conditions Using Alpha-Olefins

| Ex. | Alpha Olefin | # mol | CMR | Other | Time, hr | Temp, ° C. | Wt prod | Wt ovhd | Wt residue | physical state |
|---|---|---|---|---|---|---|---|---|---|---|
| A | $C_{14}$ | 0.1 | 0.9 | — | 4 | 190 | — | — | 14.29 | solid |
| B | $C_{14}$ | 0.1 | 0.9 | Sulf. Acid | 4 | 190 | — | — | 16.84 | solid |
| C | $C_{14}$ | 0.84 | 0.9 | — | 4 | 200 | 215.58 | — | — | solid |
| D | $C_{14}$ | 0.46 | 0.9 | — | 4 | 170 | 121.85 | — | — | solid |
| E | $C_{14}$ | 0.33 | 0.9 | Boric acid | 3 | 200 | — | 29.86 | 58.0 | solid |
| F | $C_{14}$ | 0.33 | 0.67 | — | 4 | 200 | — | 34.38 | 24.49 | solid |
| G | $C_{14}$ | 0.33 | 0.67 | Hydroquinone | 4 | 200 | — | 30.14 | 32.21 | solid |
| H | $C_{14}$ | 0.33 | 0.67 | Boric acid | 4 | 200 | — | 22.51 | 48.54 | solid |

EXAMPLE 10

Large Scale Preparation of Low Molecular Weight Branched ASAD

In a 4-liter stainless steel reactor, 1.9 kilograms (10.8 mol) of isobutylene oligomers, having a number average molecular weight of 176 atomic mass units (a.m.u.) and 73% methylvinylidene isomer content, was charged. The reactor was pressurized to 20 p.s.i.g. with nitrogen, stirred and heated to 130° C. One mole equivalent of maleic anhydride was added to the reactor over about 6 hours. The temperature was held at about 130° C. for 15 hours, and then increased to 225° C. over 7 hours. After one hour at 225° C., unreacted olefin and maleic anhydride were removed by distillation. Then the product was purified by filtration. The product yielded was a viscous, yellow oil.

EXAMPLES 11-14

A number of additional reactions of low molecular weight PIB and maleic anhydride were carried out using the procedure in example 10. The reactant PIB varied in number of carbon atoms. The results of Examples 10–14 are shown in Table 3.

TABLE 3

Additional Low Molecular Weight PIB/Maleic Anhydride Reactions' Results

| Ex. | $M_n$ | PIB | SAP no. | Vis @ 100° C. | Color | % yield | physical state | % MV* | % TSI** |
|---|---|---|---|---|---|---|---|---|---|
| 10 | 176 | $C_{8-28}$ | 441 | 21.1 | 7.5 | 84.6 | Liquid | 73 | 11 |
| 11 | 224 | $C_{16}$ | 344 | 22.3 | 2.5 | 67.1 | Liquid | 66 | 11 |
| 12 | 198 | $C_{12-28}$ | 318 | 38.4 | 4.0 | 76.8 | Liquid | 70 | 11 |
| 13 | 247 | $C_{16-28}$ | 283 | 189.1 | 6.5 | 89.2 | Liquid | 77 | 11 |
| 14 | 296 | $C_{20-28}$ | 136 | 194.4 | 3.5 | 91.6 | Liquid | 78 | 11 |

*MV = Methylvinylidene isomer
**TSI = Tri-substituted isomer

EXAMPLE 15

Preparation of ASAD Succinimdes

Low molecular weight branched ASAD from example 10, 133.1 g, 0.41 mol, was reacted with diethylene triamine, 35.71 g 0.35 mol, at 150° C. using a three neck 500 mL flask equipped with a mechanical stirrer, Dean Stark trap, condenser, and addition funnel. The amine/anhydride CMR was 0.85. After heating overnight a total of 12 mL water was recovered. To this was added 52.27 g group 2, 100N diluent oil (25% by weight). This product had 6.61% N, the total acid number was 1.59 mg KOH/g sample, and the viscosity @ 100° C. was 209 cSt. This product is shown in Table 4.

EXAMPLES 16-22

Additional succinimides were prepared using the low molecular weight ASAD using the procedure of Example 15 using different amounts of different polyamines. The results of the preparation of the additional succinimides are summarized in Table 4.

TABLE 4

Preparation of Succinimides Using Varying Amounts of Polyamines

| Ex. | Amine | Amine/ anhydride CMR | % N | TAN mg KOH/g | Vis @ 100 C., cSt |
|---|---|---|---|---|---|
| 15 | DETA | 0.85 | 6.61 | 1.59 | 209 |
| 16 | DETA | 0.5 | 4.71 | 2.48 | 111 |
| 17 | TETA | 0.85 | 8.04 | 2.48 | 121 |
| 18 | TETA | 0.5 | 5.42 | 1.81 | 181 |
| 19 | TEPA | 0.85 | 9.49 | 0.31 | 259 |
| 20 | TEPA | 0.5 | 6.58 | 1.65 | 168 |
| 21 | HPA | 0.85 | 11.4 | 1.16 | 662 |
| 22 | HPA | 0.5 | 7.94 | 1.23 | 256 |

EXAMPLE 23

A 10.0036 gram amount of ASAD from Example 2 was mixed with 0.005 grams of $C_{12}$ alkylbenzene sulfonic acid for 15 minutes. The $C_{12}$ alkylbenzene sulfonic was at 0.05%. Portions of the mixture were heated at either 150° C. or at 200° C. for either one, four or eighteen hours. The product composition was analyzed by $^1$H NMR and the composition was determined by integration of the olefin region. The composition results are reported in Table 5. Isomers (1), (2) and (3) in Table 5 refer to structures (1), (2) and (3), respectively, in Formula (B) herein.

TABLE 5

Mixed Isomer Composition Results

| Quantity Strong Acid (ppm) | Time (h) | Temp (° C.) | Isomer (1)% | Isomer (2)% | Isomer (3)% | Other Isomer % |
|---|---|---|---|---|---|---|
| 0 | — | — | 48 | 17 | 8 | 27 |
| 500 | 1 | 150 | 40 | 17 | 14 | 29 |
| 500 | 4 | 150 | 29 | 20 | 25 | 26 |
| 500 | 1 | 200 | 20 | 23 | 32 | 25 |
| 500 | 4 | 200 | 9 | 23 | 41 | 27 |
| 500 | 18 | 200 | 6 | 25 | 27 | 42 |

What is claimed is:

1. A low molecular weight branched alkenyl succinic acid derivative having the formula:

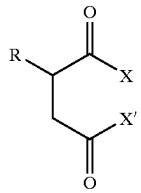

wherein

X and X' are independently selected from the group consisting of: —OH; —OR$^1$, wherein R$^1$ is alkyl of 1 to 8 carbon atoms; —NH$_2$; —Cl; —Br; and —OM+, wherein M+ is the equivalent of at least one of a metal, ammonium or alkyl ammonium cation, wherein the alkyl group has 1 to 8 carbon atoms; and X and X' when taken together are —O— or —NH——; R is a polyisobutenyl group or a mixture of low molecular weight polyisobutenyl groups having from about 8 to about 32 carbon atoms, derived from a polyisobutene having at least 50% of the methylvinylidene isomer plus trisubstituted isomer.

2. The low molecular weight branched alkenyl succinic acid derivative according to claim 1, wherein R is a polyisobutenyl group or a mixture of low molecular weight polyisobutenyl groups having from about 12 to about 28 carbon atoms.

3. The low molecular weight branched alkenyl succinic acid derivative according to claim 1, wherein R is a polyisobutenyl group or a mixture of low molecular weight polyisobutenyl groups having from about 8 to about 32 carbon atoms, derived from a polyisobutene having at least 70% of the methylvinylidene isomer plus tri-substituted isomer.

4. The low molecular weight branched alkenyl succinic acid derivative according to claim 3, wherein R is a polyisobutenyl group or mixture of low molecular weight polyisobutenyl groups having from about 8 to about 32 carbon atoms, derived from a polyisobutene having at least 80% of the methylvinylidene isomer plus tri-substituted isomer.

5. A low molecular weight branched alkenyl succinic acid derivative comprising a mixture of the following structures:

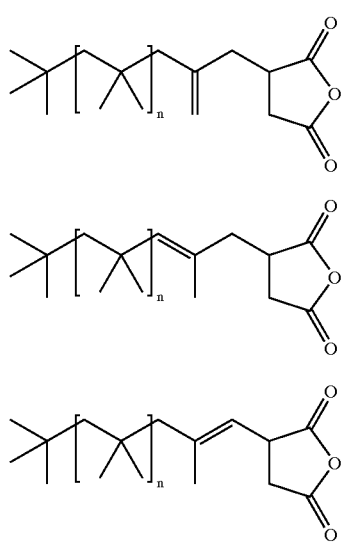

wherein n is a whole integer from 1 to 6.

6. The low molecular weight branched alkenyl succinic acid derivative of claim 5, wherein the mixture of isomers comprises from about 5% to about 60% of isomer (1), from about 10% to about 30% of isomer (2) and from about 5% to about 45% of isomer (3).

7. A process for making a low molecular weight branched alkenyl succinic acid derivative comprising:
reacting an unsaturated acidic reagent either with a low molecular weight polyisobutene having from about 8 to about 32 carbon atoms, wherein at least about 50% of the olefinic bonds of the polyisobutene comprises methylvinylidene isomer plus tri-substituted isomer, or with a mixture of low molecular weight polyisobutenes having from about 8 to about 32 carbon atoms, wherein at least about 50% of the olefinic bonds of the polyisobutenes comprises methylvinylidene isomer plus tri-substituted isomer.

8. The process according to claim 7, wherein the reaction is conducted in the presence of alkyl benzenesulfonic acid.

9. The process according to claim 7, wherein the reaction is conducted at a temperature from about 120° C. to about 240° C.

10. The process according to claim 9, wherein the reaction is conducted at a temperature from about 180° C. to about 230° C.

11. The process according to claim 7, wherein said low molecular weight polyisobutene or said mixture of low molecular weight polyisobutenes comprises one or more $C_8$, $C_{12}$, $C_{16}$, $C_{20}$, $C_{24}$, $C_{28}$, or $C_{32}$ molecules having an average molecular weight less than 300.

12. The process according to claim 7, wherein said low molecular weight polyisobutene or said mixture of low molecular weight polyisobutenes comprises one or more $C_8$, $C_{12}$, $C_{16}$, $C_{20}$, $C_{24}$, or $C_{28}$ molecules having an average molecular weight of about 120 to 300.

13. The process according to claim 7, wherein said unsaturated acidic reagent is maleic anhydride.

14. A process for making a low molecular weight branched alkenyl succinic acid derivative succinimide comprising:
(a) reacting an unsaturated acidic reagent either with polyisobutene having from about 8 to about 32 carbon atoms or with a mixture of low molecular weight polyisobutenes having from about 8 to about 32 carbon atoms and wherein at least about 50% of the olefinic bonds of either the polyisobutenes or the mixture of low molecular weight polyisobutene comprise methylvinylidene isomer plus tri-substituted isomer; and
(b) reacting the product of (a) with a polyamine.

15. The process according to claim 14, wherein said polyamine has at least 3 amine nitrogen atoms per molecule.

16. The process according to claim 15, wherein said polyamine has from about 4 amine nitrogen atoms to about 12 amine nitrogen atoms per molecule.

17. The process according to claim 16, wherein said polyamine has from about 6 amine nitrogen atoms to about 10 amine nitrogen atoms per molecule.

18. The process according to claim 14, wherein reaction (a) occurs in the presence of $C_{12}$ alkyl benzenesulfonic acid.

19. A low molecular weight branched alkenyl succinimide having the formula:

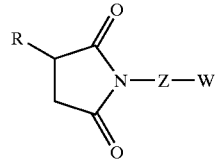

wherein W comprises one or more of:

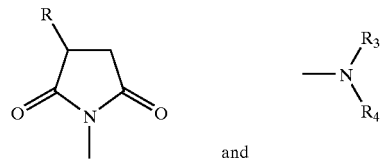

wherein R is a polyisobutenyl group having from about 8 to about 32 carbon atoms or a mixture of low molecular weight polyisobutenyl groups having from about 8 to about 32 carbon atoms derived from a polyisobutene having at least 50% of the methylvinylidene isomer plus tri-substituted isomer; Z is one or more polyamine linking radicals; and wherein $R_3$ and $R_4$ are independently hydrogen, alkyl of 1 to 10 carbon atoms, phenyl or taken together, are alkylene of 2 to 5 carbon atoms to form a ring group.

20. The composition according to claim 19, wherein R comprises one or more $C_8$, $C_{12}$, $C_{16}$, $C_{20}$, $C_{24}$, or $C_{28}$ moieties.

21. The composition according to claim 19, wherein Z is a polyamino radical having from about 3 to about 7 nitrogen atoms and from about 8 to 20 carbon atoms.

22. The composition according to claim 21, wherein Z is a polyamino radical having from about 4 to 5 nitrogen atoms and from about 8 to about 20 carbon atoms.

23. A low molecular weight branched alkenyl succinic acid derivative prepared by a process comprising:
reacting an unsaturated acidic reagent either with a low molecular weight polyisobutene having from about 8 to about 32 carbon atoms, wherein at least about 50% of the olefinic bonds of the polyisobutene comprise methylvinylidene isomer plus tri-substituted isomer, or with a mixture of low molecular weight polyisobutenes having from about 8 to about 32 carbon atoms, wherein at least about 50% of the olefinic bonds of the polyisobutenes comprise methylvinylidene isomer plus tri-substituted isomer.

24. The product produced by a process according to claim 23, wherein the reaction of the unsaturated acidic reagent either with a low molecular weight polyisobutene, wherein at least about 50% of the olefinic bonds of the polyisobutene comprise methylvinylidene isomer plus tri-susbstituted isomer, or with a mixture of low molecular weight polyisobutenes, wherein at least about 50% of the olefinic bonds of the polyisobutenes comprise methylvinylidene isomer plus tri-substituted isomer, occurs in the presence of $C_{12}$ alkyl benzenesulfonic acid.

25. The product produced by a process according to claim 23, wherein the unsaturated acidic reagent is maleic anhydride.

26. A low molecular weight branched alkenyl succinimide produced by a process comprising:
(a) reacting an unsaturated acidic reagent either with a low molecular weight polyisobutene or with a mixture of low molecular weight polyisobutenes which contain from about 8 to about 32 carbon atoms and wherein at least about 50% of the olefinic bonds of the low molecular weight polyisobutene or the mixture of low molecular weight polyisobutenes comprise methylvinylidene isomer plus trisubstituted isomer; and (b) reacting the product of (a) with a polyamine.

27. The low molecular weight branched alkenyl succinimide produced by a process according to claim 26, wherein reaction (a) occurs in the presence of $C_{12}$ alkyl benzenesulfonic acid.

28. The low molecular weight branched alkenyl succinimide produced by a process according to claim 26, wherein the unsaturated acidic reagent is maleic anhydride.

29. A lubricating oil composition comprising a major amount of an oil of lubricating viscosity and a minor amount of the succinimide of claim 19.

30. A lubricating concentrate comprising from 10 to 90 wt. % of the composition of claim 19 and from 90 to 10 wt. % of an organic diluent.

31. A fuel concentrate comprising an inert stable oleophilic organic solvent boiling in the range of from about 150° F. to 400° F. and from about 5 to about 70 weight percent of the succinimide of claim 19.

32. A lubricating oil composition comprising a major amount of an oil of lubricating viscosity and a minor amount of the succinimide of claim 26.

33. A lubricating oil composition comprising a major amount of an oil of lubricating viscosity and a minor amount of the alkenyl succinic acid derivative of claim 1.

34. A lubricating concentrate comprising from 10 to 90 wt. % of the product of claim 1 and from 90 to 10 wt. % of an organic diluent.

35. A fuel concentrate comprising an inert stable oleophilic organic solvent boiling in the range of from about 150° F. to 400° F. and from about 5 to about 70 weight percent of the product of claim 1.

36. A method of repelling liquid from the surface of a paper product comprising:
applying a liquid repelling effective amount of the alkenyl succinic acid derivative of claim 1 to the cellulose surface of the paper product in such a way that a drop of water on the surface has an initial contact angle greater than 90° and less than about 101°.

37. A friction modifying composition comprising from about 0.1 to 10 weight percent of the alkenyl succinic acid derivative of claim 1 and a major amount of oil comprising a tractor hydraulic fluid or a transmission fluid.

* * * * *

UNITED STATES PATENT AND TRADEMARK OFFICE
CERTIFICATE OF CORRECTION

PATENT NO. : 6,867,171 B2
DATED : March 15, 2005
INVENTOR(S) : James J. Harrison et al.

It is certified that error appears in the above-identified patent and that said Letters Patent is hereby corrected as shown below:

<u>Title page,</u>
Item [73], Assignee, change "Oronitz" to -- Oronite --

Signed and Sealed this

Twenty-fourth Day of May, 2005

JON W. DUDAS
*Director of the United States Patent and Trademark Office*